United States Patent

Netherly et al.

[11] Patent Number: 5,836,942
[45] Date of Patent: Nov. 17, 1998

[54] BIOMEDICAL ELECTRODE WITH LOSSY DIELECTRIC PROPERTIES

[75] Inventors: Samuel G. Netherly, Afton; Hatim M. Carim, West St. Paul, both of Minn.

[73] Assignee: Minnesota Mining and Manufacturing Company, St. Paul, Minn.

[21] Appl. No.: 628,182

[22] Filed: Apr. 4, 1996

[51] Int. Cl.⁶ .............................. A61B 17/39; A61N 1/04
[52] U.S. Cl. ............................. 606/32; 606/35; 607/142; 607/149; 607/152; 29/829
[58] Field of Search ..................... 606/32, 35; 607/142, 607/149, 152, 153; 29/829

[56] References Cited

U.S. PATENT DOCUMENTS

| | | | |
|---|---|---|---|
| 4,669,468 | 6/1987 | Cartmell et al. | 606/32 |
| 4,736,752 | 4/1988 | Munck et al. | 607/152 |
| 4,893,626 | 1/1990 | Henley et al. | 128/640 |
| 5,178,957 | 1/1993 | Kolpe et al. | 428/458 |
| 5,205,297 | 4/1993 | Montecalvo et al. | 128/798 |
| 5,211,174 | 5/1993 | Imran | 128/639 |
| 5,402,884 | 4/1995 | Gilman et al. | 206/328 |
| 5,456,710 | 10/1995 | Gadsby | 607/142 |

FOREIGN PATENT DOCUMENTS

| | | |
|---|---|---|
| 327304 | 8/1989 | European Pat. Off. ............ 607/152 |
| 40 13 188 A1 | 11/1990 | Germany . |
| 40 35 247 A1 | 5/1992 | Germany . |
| WO 87/05814 | 10/1987 | WIPO . |
| WO 93/21989 | 4/1993 | WIPO . |
| WO 95/31145 | 11/1995 | WIPO . |

OTHER PUBLICATIONS

Derwent Abstract for PCT Publication WO 87/05814 (1987).
Derwent Abstract for DE 40 35 247 A1 (1992).

Primary Examiner—Lee S. Cohen
Attorney, Agent, or Firm—John H. Hornickel

[57] ABSTRACT

A biomedical electrode having an electrically non-conductive backing and at least one, and preferably two, conductive plates contacting the electrically non-conductive backing. A field of lossy dielectric material is used between the electrically conductive plate(s) and the surface of the electrode applied to a patient. A field of conductive adhesive contacts both the conductive plate(s) and the field of lossy dielectric material. The electrode does not operate purely capacitively, nor does it operate purely resistively. Hot spots due to "edge effect" are substantially reduced. At the same time, the biomedical electrode functioning as a electrosurgical dispersive electrode has an impedance within the range expected by the contact monitoring safety circuits provided with many current electrosurgical generators. The biomedical electrode also can function as a cardiac stimulating electrode, such as a defibrillation, cardioversion, or pacing electrode. A method of controlling the lossy dielectric properties of the biomedical electrode is also disclosed.

18 Claims, 5 Drawing Sheets
(3 of 5 Drawing Sheet(s) Filed in Color)

BIOMEDICAL ELECTRODE WITH LOSSY DIELECTRIC PROPERTIES

TECHNICAL FIELD

The present invention relates generally to biomedical electrodes of the type that delivers to or receives currents from a body, such as dispersive electrodes used to return current from a patient's body in electrosurgery or cardiac stimulating electrodes used to deliver current to a patient's body.

BACKGROUND

Biomedical electrodes are used in a variety of applications and are configured to operate according to the size, type, and direction of current flowing into or out of a body of a patient.

Dispersive electrodes are used in electrosurgery. In modern surgical practice there are many times when electrosurgery is more preferable than the use of the traditional scalpel. In electrosurgery, cutting is performed by an intense electrical current passing through a cutting electrode. The surgeon directs this current to exactly where cutting is required by wielding the cutting electrode, which because of its cylindrical shape and the way it is held in the hand is commonly called an "electrosurgical pencil". By activating controls which change the characteristics of the electrical current being sent to the pencil by an electrosurgical generator, the surgeon can use the pencil either to cut or to coagulate areas of bleeding. This makes electrosurgery particularly convenient when surgery requiring extra control of blood loss is being performed. Because of concerns to minimize the transmissions of blood-borne illnesses between health care patients and health care providers, in both directions, electrosurgery is becoming increasingly important.

In electrosurgery, as in all situations where electrical current is flowing, a complete circuit must be provided to and from the current source. In this case, the current that enters the body at the pencil must leave it in another place and return to the generator. It will readily be appreciated that when current enough to deliberately cut is brought to the body of a patient in one place, great care must be taken that unintentional damage is not also done to the patient at the location where that current is leaving the body. The task of collecting the return current safely is performed by a dispersive electrode.

A dispersive electrode performs this task by providing a large surface area through which the current can pass; the same current which was at cutting intensity when focused at the small surface area at the tip of the pencil is relatively harmless, with the goal of being painless to the patient, when spread out over the large surface area of the dispersive electrode.

There are two major known types of dispersive electrodes, characterized by the predominant type of electrical phenomenon taking place where the electrode contacts the body. Each of the two types has competing advantages and disadvantages.

The first type is known as the resistive type of dispersive electrode, since resistance phenomena are responsible for the current transfer between the body of the patient and the electrode. A disadvantage of this type of dispersive electrode is that it has a so-called "edge effect"; the current density is much higher at the corners and edges than at the center of the electrode. Thus, the maximum temperature rise in patient tissue for this type of electrode is much greater than for a theoretically "perfect" resistive electrode where the current would be evenly distributed over the entire conductive surface area. If a theoretically "perfect" resistive electrode were to be constructed that caused the same maximum temperature rise in patient tissue as a commercially available resistive electrode as presently manufactured, the "perfect" electrode would be substantially smaller in size because of its ability to uniformly distribute the current flowing from the body of the patient into the conductive surface of the electrode contacting the patient.

An advantage of the resistive type of dispersive electrode is that the adequacy of the contact between the electrode and the patient's body can be monitored by contact quality monitoring ("CQM") circuitry in the electrosurgical generator. Many of the most popular generator systems have safety circuits which can detect when a resistive electrode does not have good attachment to the body. If some mischance in the surgical suite has caused the electrode to be applied without adequate initial contact with the body or some event during surgery has caused the adequate initial contact to become inadequate, these safety circuits will detect that problem and refuse to let any cutting current be applied or continued.

The second type of dispersive electrode is known as the capacitive type, since capacitance phenomena are responsible for the current transfer between the body of the patient and the electrode. An advantage of this type of dispersive electrode is that it does not have the edge effect of concern for resistive type dispersive electrodes, and in normal use the current transfer is much more uniform across the surface of the electrode compared to resistive types.

A disadvantage of capacitive electrodes is they are not compatible with the above described CQM circuits, and thus when used do not have this protection against inadvertent misapplication.

From the foregoing, it is clear that the art requires a dispersive electrode which has both a very uniform distribution of the current across its surface while at the same time is suitable for being monitored against the hazard of accidental detachment.

Uniform distribution of current density has been studied with respect to stimulating electrodes, where electrical energy is being delivered to a patient via a biomedical electrode. Representative of these studies is Kim et al., "Uniformity of Current Density Under Stimulating Electrodes" *Critical Reviews in Biomedical Engineering* Vol. 17, Issue 6 pp. 585–619 (1990). Electrodes for stimulation of the heart, i.e., pacing electrodes have also been concerned with area resistivity. U.S. Pat. No. 4,776,350 (Grossman et al.) has disclosed an electrode that has differing resistivities between different conductive members on the electrode.

Defibrillation, cardioversion, and pacing electrodes are used to deliver current to a body of a patient with sufficient power to reach and alter performance of the myocardial muscles of the heart. Distribution of current density for these types of cardiac stimulating electrodes is critical to the performance of the electrodes for their intended functions: to cause the heart to change its pattern of beating.

SUMMARY OF THE INVENTION

The present invention solves the problems discussed above by providing a biomedical electrode in which one can control current density at the electrode/body interface.

The biomedical electrode of the present invention has a "lossy dielectric" region over a part of the electrode/body interface.

Unexpectedly, the "lossy dielectric" properties of the biomedical electrode solves problems that confront both resistive-type and capacitive-type dispersive electrodes and cardiac stimulating electrodes such as defibrillation, cardioversion, and pacing electrodes. Edge effect common to resistive type dispersive electrodes and cardiac stimulating electrodes is substantially reduced. Yet the electrode of the present invention provides acceptable CQM performance, which is unavailable in capacitive type dispersive electrodes with sufficient accuracy.

For purposes of this invention, "lossy dielectric" properties mean that biomedical electrodes have a conductor surface that has performance parameters between the extremes of (1) a resistive-type dispersive electrode that provides an edge effect at its periphery of a conductive surface; and (2) a capacitive-type dispersive electrode that provides only capacitive current flow between the conductive surface and the body of a patient, i.e., providing almost totally uniform current density over the conductive surface.

Cardiac stimulating electrodes are resistive-type electrodes that cause an edge effect similar to resistive-type dispersive electrodes. Avoidance of edge effect in cardiac stimulating electrodes is an advantage of the present invention by helping to avoid needless discomfort for the patient undergoing such cardiac stimulation through extracorporally-placed electrodes.

Nonlimiting examples of performance parameters that can be used to characterize a "lossy dielectric" biomedical electrode include (a) the resistive skin contacting area of the conductive surface (through conductive adhesive) compared with the area of the total conductive surface of the biomedical electrode;

(b) at specified frequencies, the electrical impedance gradient from the center of the conductive surface to the edge of the conductive surface;

(c) the maximum impedance at the edge of the conductive surface of the electrode;

(d) the average current density levels at given levels of amplitude and frequency of electrical energy to be dispersed;

(e) the resistance component of impedance of the conductive surface at determined locations on the biomedical electrode;

(f) the reactance component of impedance of the conductive surface at determined locations on the biomedical electrode; and (g) the tan δ, that divides the resistance component of impedance by the reactance component of impedance, at determined locations on the biomedical electrode.

"Reactance" is the electrical resistance offered by a capacitor to current flow at a given frequency.

Therefore, lossy dielectric materials occupy that region between pure capacitance and pure resistance and have a δ of >0° and <90°.

This invention employs lossy dielectric materials in dispersive electrodes, a field previously dominated by either resistive-type electrodes or capacitive-type electrodes.

This invention also employs lossy dielectric materials in cardiac stimulating electrodes, such as defibrillation, cardioversion, and pacing electrodes.

Tan δ has also been used to determine the anti-corroding properties of paint in industrial fields.

Each of the above performance parameters mean little to the patient unless the biomedical electrode actually minimizes the maximum amount of temperature rise at a determined location(s) on the biomedical electrode when in use. However, use of a combination of the above performance parameters can provide a biomedical electrode of the present invention that minimizes the maximum amount of temperature rise in tissue of a patient in contact with a biomedical electrode of the present invention.

One aspect of the invention is a biomedical electrode that has a maximum rise in temperature of less than 6° C. from beginning of usage with an electrosurgical generator, when tested according to industry testing standard "AAMI Standard Section 4.2.3.1, Maximum Safe Temperature Rise" (Association for the Advancement of Medical Instrumentation, 1986).

Another aspect of the invention is a dispersive electrode having a rise in temperature of the dispersive electrode during usage with an electrosurgical generator that is proportional to a maximum current density.

Another aspect of the invention is a biomedical electrode having the same or lower maximum temperature rise performance as a larger biomedical electrode.

Another aspect of the invention is a dispersive electrode that has a more uniform temperature profile, beneficially similar to a capacitive-type dispersive electrode, and an ability to respond to CQM monitoring via its non-periphery skin-contacting portion, beneficially similar to a resistive-type dispersive electrode.

Preferably, a biomedical electrode of the present invention has an electrically non-conductive backing and at least one conductive plate adjacent to the electrically non-conductive backing. In many of the most preferred embodiments, there will be two conductive plates which lie adjacent to each other with both adhered to the electrically non-conductive backing. There is a field of lossy dielectric material between the conductive plate and a surface of the electrode contacting a body of a patient. A field of conductive adhesive will be present, in contact with both the conductive plate(s) and the field of lossy dielectric material.

It is particularly convenient to provide this biomedical electrode so that the conductive plates have a body contacting portion and an extended tab. This arrangement allows for easy connection to conventional electrosurgical generators. Most preferably, the field of lossy dielectric material contacts a region adjacent the exterior edge of the body contacting portion.

Embodiments of the invention are described using the following drawings.

BRIEF DESCRIPTION OF THE DRAWING

The file of this patent contains at least one drawing executed in color. Copies of this patent with color drawings will be provided by the Patent and Trademark Office upon request and payment of the necessary fee.

The reference numerals refer to like parts in the several views, and wherein.

EMBODIMENTS OF THE INVENTION

Figure 1:
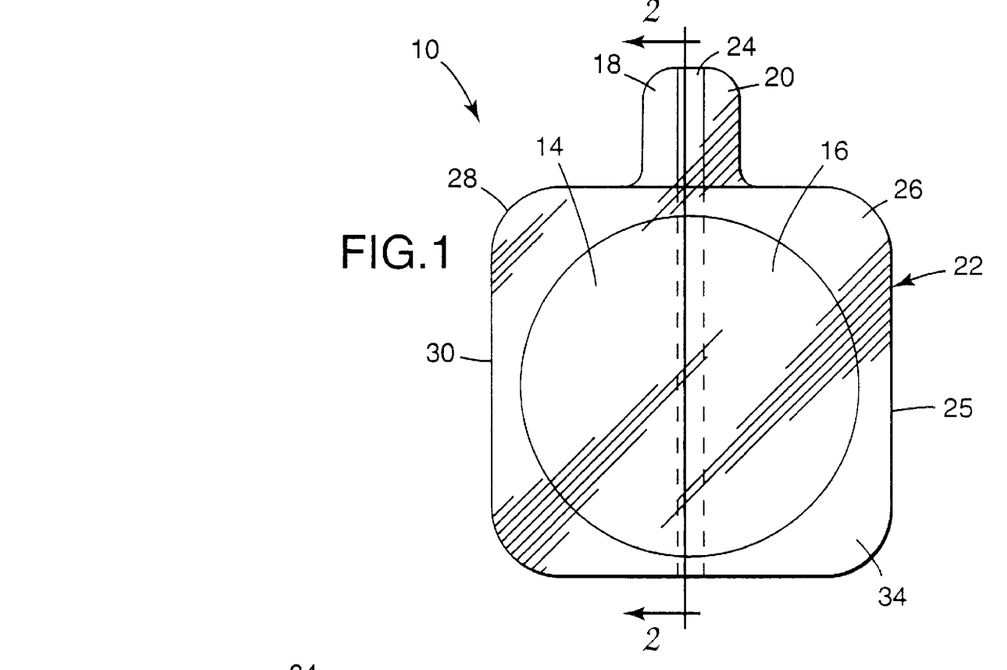
FIG. 1 is bottom perspective view according to one presently preferred embodiment of the dispersive electrode of the present invention.

FIG. 1 shows a bottom perspective view of the dispersive electrode 10. The upper surface of the electrode 10, which is on the far side in this bottom view, can be a flexible and conformable electrically non-conductive backing 12. Two conductor plates 14 and 16 are present, adjacent to, and can be adhered to, the electrically non-conductive backing 12. Providing two separate conductor plates is not a requirement of the invention, but is convenient in many preferred embodiments because the impedance between the conductor plates 14 and 16 is measured by several of the above mentioned CQM circuits. Only dispersive electrodes having two conductor plates and being in adequate contact with the body of a patient will provide the impedance expected by the CQM circuits.

Each of the two conductor plates 14 and 16 has an extended tab 18 and 20, respectively, extending away from the body contact portion 22 of the electrode 10 for the attachment of a cable assembly which connects the electrode 10 to an electrosurgical generator (not shown). In order to provide more support for the conductor plates 14 and 16, and especially for their respective tabs 18 and 20, a non-conductive support layer 24 can be laminated to the conductor plates.

The region adjacent the exterior edge 25 of the body contact portion 22 of the electrode 10 can be covered with a layer 26 of a lossy dielectric material. In the embodiment of FIG. 1, the width of the layer 26 of a lossy dielectric material is widest at the corners 28, and narrowest along the edge 30 midway between the corners. As presently understood, this arrangement of the layer 26 serves best to reduce edge effect at the corners 28 of the dispersive electrode.

Preferably, the entire body contact portion 22 of electrode 10 is covered with a field 32 of conductive adhesive. Many compositions suitable for use for the field 32 of conductive adhesive are transparent, or at least translucent, and have been depicted that way in FIG. 1 for convenience in providing an explanatory drawing. The field 32 of conductive adhesive serves the dual purposes of adhering the electrode 10 to the body of the patient and of transferring the electrosurgical current between the body of the patient and the electrode for electrosurgical currents and between the electrode and the body for CQM monitoring.

Figure 2:
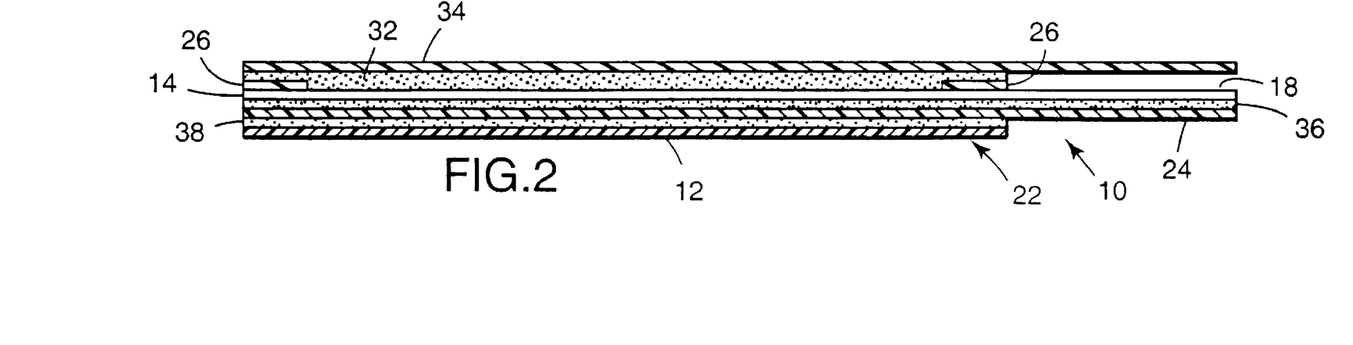
FIG. 2 is a cross-section view which is taken along section lines 2—2 in FIG. 1.

FIG. 2 shows a cross-section view of the electrode shown in FIG. 1, taken along section lines 2—2. In this view, a release liner 34 is shown adhered to the field 32 of conductive adhesive This release liner 34 protects the conductive adhesive during shipping and handling and is removed just prior to use. In this view a layer of adhesive 36 is seen adhering the support layer 24 to conductor plate 14 and its extended tab 18. Another layer of adhesive 38 is provided for adhering the electrically non-conductive backing 12 to the other side of the support layer 24.

Electrically non-conductive backing

Electrically non-conductive backing 12 can be electrically insulative, and preferably is very conformable to the human body. Many materials can be used for this purpose, as will be apparent to those skilled in the art. In one presently preferred embodiment, a closed-cell foam is considered particularly suitable. One such material is commercially available as Volara brand foam from Voltek, Inc. of Massachusetts. The electrically non-conductive backing can have a thickness ranging from about 0.75 mm (0.03 inch) to about 1.5 mm (0.06 inch), and preferably 1.0 mm (0.04 inch).

Conductor plates and support layer

The conductor plates 14 and 16 are conveniently made from metal, preferably in the form of a foil; a metal-containing or graphite-containing coated ink or pain, or a vapor coated metal, and most preferably, aluminum foil. If a support layer 24 is not being used, a thickness of about 0.08 mm (0.0003 inch) is considered preferred. If a support layer 24 is being used, the metal foil or vapor coated metal can be thinner because of the support provided by the support layer. A suitable support layer 24 can be made from polyethylene terephthalate (PET) film, conveniently approximately 0.05 mm (0.002 inch) thick. This allows the aluminum layer to range in thickness between about 0.0075 mm (0.0003 inch) to about 0.025 mm (0.001 inch) and preferably 0.012 mm (0.0005 inch) or allows vapored coated metal to have a minimum thickness of about 1000 Angstroms. An example of vapored coated metal on a substrate is found in PCT Publication No. WO 94/26950, the disclosure of which is incorporated by reference herein.

Conductive adhesive

Nonlimiting examples of conductive adhesives useful in connection with the present invention include those compositions disclosed in U.S. Pat. Nos. 4,524,087 (Engel); 4,539,996 (Engel); 4,848,353 (Engel) and 5,133,356 (Bryan et al),; 5,225,473 (Duan); 5,276,079 (Duan et al); 5,338,490 (Dietz et al); 5,362,420 (Itoh et al); 5,385,679 (Uy et al); copending and coassigned applications PCT Publication Nos. WO 95/20634 and WO 94/12585; and PCT patent application Ser. Nos. US95/17079 (Docket No. 51537PCT6A); US95/16993 (Docket No. 51290PCT8A); and US95/16996 (Docket No. 48381PCT1A), the disclosures of which are incorporated by reference herein.

Release liner

Release liner 34 can be any construction suitable for protecting the conductive adhesive 32 during shipping and handling while still releasing easily from the conductive adhesive at the time of use. One suitable liner is a 0.05 mm (0.002 inch) thick sheet of biaxially oriented polypropylene liner, commercially available as Daubert 164Z from Daubert Co. of Dixon, Ill.

Adhesive layers

In some presently preferred embodiments, adhesive layers 36 and 38 may be used for holding other components of the electrode 10 together. Nonlimiting examples suitable adhesives 36 and 38 include acrylate ester adhesives, and more particularly acrylate ester copolymer adhesives. Such adhesives are generally described in U.S. Pat. Nos. 2,973,826; Re 24,906; Re 33,353; 3,389,827; 4,112,213; 4,310,509; 4,323, 557; 4,732,808; 4,917,928; 4,917,929; and European Patent Publication 0 051 935, all incorporated herein by reference.

Optionally, such adhesives can also be used to provide a border of pressure sensitive adhesive on the exterior edge 25 of electrode 10, as is disclosed in U.S. Pat. Nos. 4,524,087 (Engel); 4,539,996 (Engel); 4,848,353 (Engel).

Lossy dielectric layer

The layer 26 of lossy dielectric material has the performance parameters identified above in association with the ultimate performance of electrode 10 to minimize the maximum rise in temperature of tissue of a patient during electrosurgical procedures.

The lossy dielectric layer 26 can occupy an area of the body contact portion 22 ranging from about 5% to about 70% and preferably from about 40% to about 60%.

The lossy dielectric layer 26 can be made from a material and be applied in a non-uniform thickness to result in an electrical impedance gradient from the center of the body contact portion 22 to the exterior edge 25 ranging from about 30% to about 90% of the maximum impedance at exterior edge 25, and preferably from about 50% to about 70% of the maximum impedance at exterior edge of body contact portion 22.

The layer 26 can have a maximum impedance/area at the exterior edge 25 of the body contact portion 22 of the electrode 10 ranging from about $0.387\Omega/129$ cm$^2$ to about $20\Omega/129$ cm$^2$ and preferably ranging from about $1\Omega/129$ cm$^2$ to about $8\Omega/129$ cm$^2$, as determined by use of a Schlumberger 1260 spectrum impedance analyzer, operating at a frequency of 500 kHz and a constant voltage of 60 mV (RMS), and subjected to a nulling file to subtract out the effects of leadwires, connecting clips, and test fixture. A dispersive electrode of approximately 129 cm$^2$ (20 in$^2$) is the approximate size of most commercially available dispersive electrodes.

The layer 26 can have a resistance component per unit area (R/area) of the complex impedance Z of from about $0.4\Omega/129$ cm$^2$ to about $5\Omega/129$ cm$^2$ at exterior edge 25 on the dispersive electrode 10. Preferably, the layer 26 can have a resistance component per unit area ranging from about $0.5\Omega/129$ cm$^2$ to about $1.4\Omega/129$ cm$^2$. These values were determined as done for the maximum impedance per unit area.

The layer 26 can have a reactance component per unit area (X/area) of the complex impedance of from about $-0.5\Omega/129$ cm$^2$ to about $-16\Omega/129$ cm$^2$ at exterior edge 25 on the dispersive electrode 10. Preferably, the layer 26 can have a reactance component per unit area ranging from about $-2\Omega/129$ cm$^2$ to about $-10\Omega/129$ cm$^2$, using the same testing method as above for resistance per unit area and impedance per unit area.

The layer 26 can have a tan δ ranging from about 0.14 to about 1.7 at exterior edge 25 on the electrode 10, when measured at 500 kHz and a signal amplitude of 60 mV (RMS). Desirably, the tan δ can range from about 0.2 to about 1.0 at exterior edge 25 on the electrode 10, when measured at 500 Hz and a signal amplitude of 60 mV (RMS). Preferably, the tan δ ranging from about 0.2 to about 0.7 at exterior edge 25 on the electrode 10, when measured at 500 Hz and a signal amplitude of 60 mV (RMS).

Layer 26 can be made from any lossy dielectric material that can be applied to body contact portion 22 and provide the performance parameters identified above for layer 26.

Layer 26 can be formed from an ink or paint on body contact portion 22 according to electrode manufacturing techniques known to those skilled in the art. It has been found particularly convenient to provide this material in the form of a paint, which can then be screen printed or sprayed in an appropriately shaped pattern onto the electrode 10 at the proper time during its fabrication. Oil-based enamels, commercially available as Cat. nos. 7776, 7790, 7730, 7727, and 7715 from Rust-oleum Corp. of Vernon Hills, Ill. are considered particularly suitable. Inks such as Summit UVII 300, UVII 800, and UVII 801 white inks, from Summit, Inc. of North Kansas City, Mo. can also be used.

Method of Making Electrodes

Electrode 10 can be made using conventional tab/pad style electrodes as described in U.S. Pat. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); 5,215,087 (Anderson et al.); and 5,296,079 (Duan et al.), the disclosures of which are incorporated by reference herein. Generally, multiple layered electrode 10 can be assembled from rolls of starting materials for insulative electrically non-conductive backing 12, upon which is applied conductor plates 14 and 16, upon which is coated paints or inks to form lossy dielectric layer 26, upon which is coated or cured field 32 of ionically conductive pressure sensitive adhesive. Alternatively, a sheet of lossy dielectric material of a desired geometrical shape can be laminated onto conductor plates 14 and 16.

Automated machinery can be employed to make electrode 10. One skilled in the art of making electrodes can select from a variety of machinery manufacturers and manufacturing techniques to minimize manufacturing expense and waste. Some types of machinery are disclosed in U.S. Pat. Nos. 4,715,382 (Strand); 5,133,356 (Bryan et al.); and copending, coassigned U.S. patent application Ser. No. 08/343,253 (Yasis et al.), the disclosures of which are incorporated by reference herein, and U.S. Pat. No. 5,352,315 (Carrier et al.).

Method of Controlling Lossy Dielectric Properties on Biomedical Electrodes

The choice of lossy dielectric material for a particular biomedical electrode application can be made based on tan δ for a given dielectric material.

As stated previously, reactance and resistance components of the dielectric material are compared at a given frequency of interest, to determine tan δ, which is a dimensionless value independent of size of the biomedical electrode.

Thus normalized, the determination of tan δ for any material can be used to control dielectric properties of the biomedical electrode or any location or region of the biomedical electrode where lossy dielectric properties are desired.

Use of tan δ is based on the following analysis.

For a sinusoidal signal of frequency "F" Hertz passing through a capacitor of "C" Farads, the resistance offered to the flow of current is called the reactance, measured in units of Ohms. Reactance is a positive value if it is due to an inductance; it is a negative value if due to a capacitance. If the resistance of a piece of material is "R" Ohms, and if it has a capacitance of "C" Farads, the reactance due to the capacitance is $X_c = -1/(2*\pi*F*C)$ Ohms.

The impedance is Z=R−jX, where j denotes the imaginary component X of the complex impedance Z. The real component is R. Tan δ is the ratio of R/|X|, where |X| denotes the magnitude of −X or +X.

If measured complex impedance has no capacitance (i.e., pure resistance) and hence −jX=0, then Z=R and tan δ=90°. If measured complex impedance has no resistance (i.e., pure capacitance), then R=0 and δ=0°.

By convention known to those skilled in the art, capacitance is identified by the equation:

$$C = (\epsilon_r * \epsilon_o)(A/d)$$

where $\epsilon_r$=relative permittivity of the dielectric material being analyzed between the plates of a capacitor "C", $\epsilon_o$=permittivity of free space ($8.85 \times 10^{-12}$ F/m), A=area of plates, and d=distance between plates.

It can be shown that relative permittivity, $\epsilon_r$, can be a complex quantity such that $\epsilon_r = \epsilon' - j\epsilon''$. Then the current, "i" flowing through the lossy dielectric material consists of an "in phase" component "$i_L$" through a pure resistor "$r_p$" and an imaginary capacitive component current "$i_c$" through, a pure capacitor "$c_p$" in parallel to the pure resistor. It can then be shown that the phase angle, tan δ, between "i" and "$i_c$" is such that $$\tan \delta = |i_L|/|i_c| = \epsilon''/\epsilon'$$

If the dielectric material is loss free, then $\epsilon''=0$. Otherwise, $\epsilon''$ is a measure of the performance of a dielectric material as an electrical insulator and is also known as the dielectric conductivity.

$$\delta = \arctan(\epsilon''/\epsilon').$$

Any circuit with a resistor $r_p$ and a capacitor $c_p$ in parallel can be represented by as an equivalent circuit of a resistor, $r_s$, in series with a capacitor, $c_s$.

For a parallel circuit, $$\tan \delta = 1/\omega * r_p * c_p$$

with the equivalent series being, $$\tan \delta = \omega * r_s * c_s$$

where $\omega = 2*\pi*F$.

Those skilled in the art are also directed to Anderson, *Dielectrics* (Chapman & Hall, London, 1967 pp. 14–28, 39–48), the disclosure of which is incorporated by reference.

When a material is characterized by modelling it as a parallel circuit, then it is usually evaluated in terms of its admittance, Y, defined as the inverse of its impedance, Z. Conversely, evaluation of circuit elements in series uses impedance, Z.

Dielectric properties discussed above are true for a given frequency, f, considering $\epsilon_r$ is represented by a pure capacitor, $c_p$, in parallel with a pure resistor, $r_p$. In practice, however, $\epsilon''$ and $\epsilon'$ are functions of frequency, i.e., the parallel equivalent circuit is only good at one frequency. The frequency dependence of $\epsilon_r$ is known as "dielectric relaxation."

The simple measurement of impedance, Z, at frequency, f, is $$Z = r_s + (1/j*\omega*c_s) = r_s - (j/\omega*c_s)$$

and $$\delta = \arctan(\omega * r_s * c_s)$$

These two equations are considered good estimates of the real frequency dependent $\epsilon_r$ for the purpose of comparing various lossy dielectric materials in the biomedical electrodes of the present invention. Thus, one skilled in the art can control the lossy dielectric properties of the biomedical electrode with this information to determine tan δ for that material.

Usefulness of the Invention

Biomedical electrodes can be constructed from a variety of lossy dielectric materials in a variety of geometries and sizes according to the desired uses of the electrodes by those skilled in the art.

The embodiments of FIGS. 1 and 2, and the graphs and thermograms of FIGS. 3–6, illustrate how one can use the scope of the present invention to make a useful dispersive electrode.

However, the same principles can be used to determine the appropriate lossy dielectric material, electrode geometry and size, etc., for the construction and usage of a cardiac stimulation electrode.

For example, one can provide a differential in distances between conductor plates 14 and 16 on backing 12. One can create a concave non-conductive area between plates 14 and 16 while still providing cooperation with CQM monitoring. Indeed, cooperation with CQM monitoring could be enhanced by such concave area between plates 14 and 16, for those occasions when tension on an extended tab of the electrode 10 causes the electrode to begin to lift from the body of the patient, creating an alarm situation during CQM monitoring. The concave area will cause the electrode to reach the CQM alarm condition during CQM monitoring with less total separation of the electrode from the body of the patient and thus further protect the patient from unacceptable maximum tissue temperature rise.

In a defibrillation electrode, used where the myocardial muscle in fibrillation needs an immediate, stabilizing delivery of intense current, one can control the current density of any region of the cardiac stimulation electrode by use of lossy dielectric material in order to concentrate the delivery of the current to penetrate into the body for immediate defibrillation.

In a cardioversion electrode, the amount of current desired for the procedure may differ from defibrillation current requirements, causing a desire to revise the choice of the lossy dielectric material, its geometry or size on the electrode, and the like to provide the correct amount of current to the myocardial muscle to alter arhythmias.

In a pacing electrode, the amount of current desired for the procedure may also differ from either the defibrillation electrode or the cardioversion electrode, causing a desire to revise the choice of the lossy dielectric material, its geometry or size on the electrode, and the like to provide the correct amount of current to the myocardial muscle to provide efficacious external pacing.

Thus, one can control the distribution pattern and magnitude of current density in the tissue volume of the patient's body under an electrode.

Embodiments of the invention are further described in the following examples.

EXAMPLE 1

An electrode was constructed from a 129 cm$^2$ cm (20 square inches) of Aluminum foil with an electrically insulating material, flat black spray paint (No. 7776 from Rustoleum Corporation), sprayed from about 20 cm (8 inches) between spray nozzle and electrode surface, at the edge of the return electrode, resulting in the edge between resistive and lossy dielectric regions of the electrode surface becoming much less resistively conductive. However, due to the dispersion of the spray from the outer edge of the electrode, there was a gradual transition from 100% electrically insulating coverage at the outer edge of the electrode to no coverage in the middle of the electrode.

A layer of conductive adhesive was prepared according to the following procedure. Into a 300 gallon kettle equipped with overhead stirrer and a cooling jacket was charged 562.8 pounds (255.5 kg) acrylic acid, 1.4 pounds (636 grams) 2,2-dimethoxy-2-phenyl acetophenone, 2.8 pounds (1273 grams) 4-(2-hydroxyethoxy)phenyl-(2-hydroxy-2-methylpropyl)ketone, 1.12 pounds (508 grams) methylene bis(acrylamide), 1251.6 pounds (568.2 kg) glycerin, 2.8 pounds (1273 grams) guar gum, and 459.6 pounds (208.7 kg) deionized water. To the well stirred solution was charged 499.8 pounds (226.9 kg) 50% aqueous NaOH portionwise maintaining the batch temperture below 38° C. The hydroxide line was rinsed into the kettle with an additional 18 pounds (8.2 kg) deionized water and stirred for 30 minutes to yield coater-ready precursor. The precursor was coated onto the foil side of a polyester/aluminum foil laminate at 23 mil (0.6 mm) thick, overlaminated with a siliconized polyester liner, and passed through a curing chamber consisting of banks of fluorescent "black" lights, exposing the material to an intensity of 1.9 mW/sqcm and a total dose of 315 mJ/sqcm.

The layer of conductive adhesive so prepared was then placed over the whole square of the electrically conductive surface. This electrode was placed on an anterior thigh of a human and energized according to the AAMI standard for thermography: 4.2.3.1, "Maximum Safe Temperature Rise" (1986).

The electrode was then removed and the heating pattern observed by placing a liquid crystal film over the anterior thigh area.

There was no sign of any real edge effect around the circumference of the electrode between resistive and lossy dielectric regions. The construction of Example 1 clearly achieved a reduction of edge effect compared to a commercially available dispersive electrode.

EXAMPLES 2–6

Several more samples were prepared which visually had different coverages and patterns of spray paint but otherwise in accordance with Example 1. When electrodes prepared according to these Examples 2–6 were tested according to the same AAMI standard on the same anterior thigh of the same human patient, the reduction in edge effect was proportional to the completeness with which the flat black paint covered the outer edge of the electrode.

EXAMPLE 7

Figure 3:
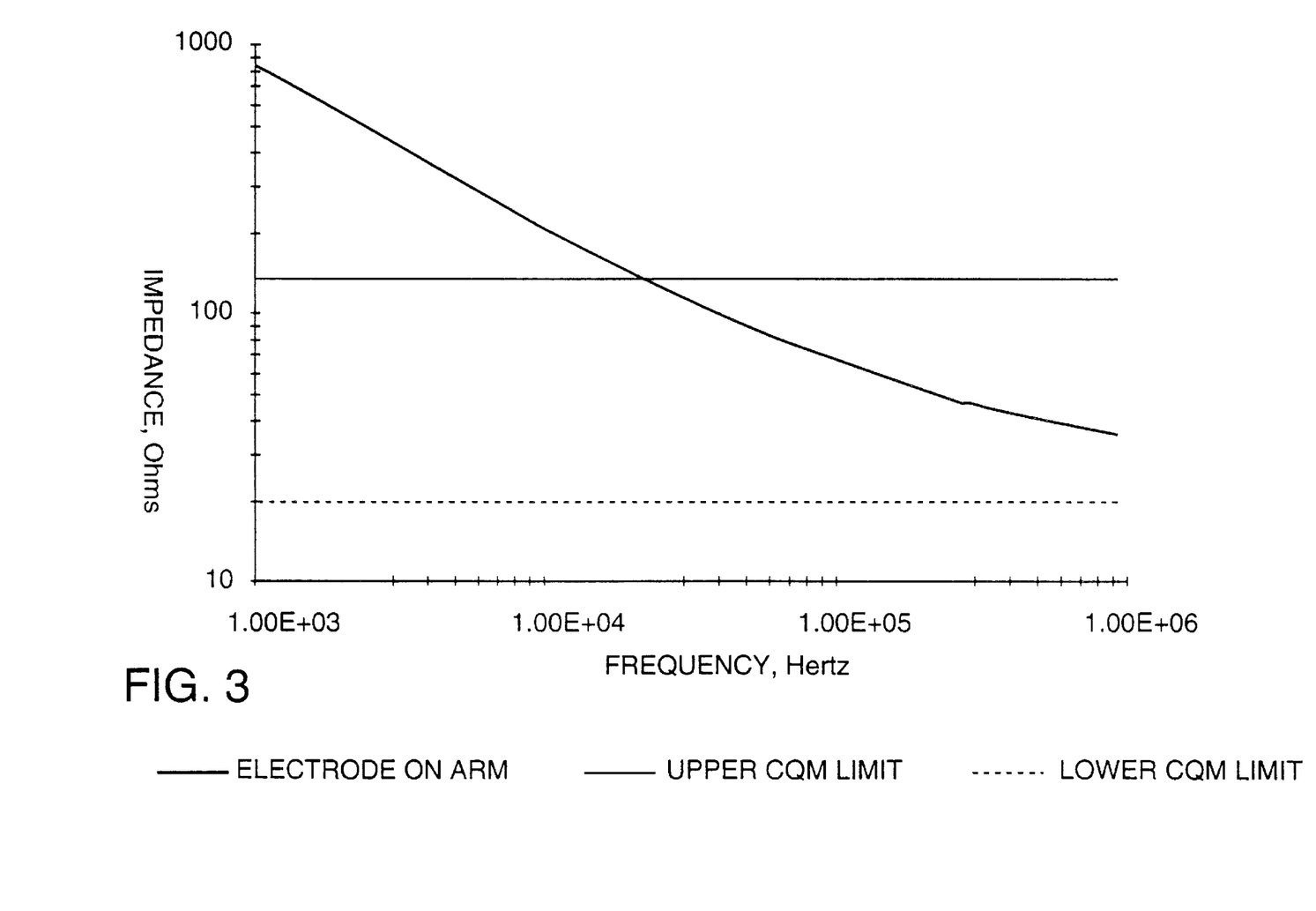
FIG. 3 is a graph of impedance in Ohms and frequency in Hertz plotted for dispersive electrodes of the present invention applied to a human arm and tested for CQM acceptance.

To prove that CQM compatibility existed in an electrode of the present invention, an electrode was prepared according to Example 1, and a 0.06 mm (¼") wide strip was then cut out of the aluminum foil along the midline of the electrode. This electrode was then applied to a forearm of the same human, and an alternating current (AC) impedance scan was between the two conductors of this split return electrode from 1 MHZ to 1 Hertz. In the range from 350 KHz to 25 KHz, the AC impedance was measured from 55 to 124 ohms, which is within the CQM limits of all major electrosurgical generator manufacturers. FIG. 3 provides the graphical results.

EXAMPLES 8–14

Electrodes were prepared according to Example 2 above, except that the outer border was completely and uniformly covered in the same paint, with an abrupt transition to the bare Al metal center about 1 cm in from the outer edge of the electrode, rather than a gradual shading as occurred in the spraying of electrodes in Examples 2–6.

Thermograms of these electrodes showed that, unexpectedly, there was also a reduction of the temperature at the external edge of the electrode.

Moreover, with an electrode that had a substantially uniform covering of spray paint over the whole surface of the Al foil, the thermogram did not show a thermal pattern typical of a capacitive plate.

These data demonstrated that the nature of the shading of the electrically insulating paint was not the sole reason for a reduction in edge effect, and further, that the paint was also not acting as a capacitive layer.

Analysis of the paint using a Schlumberger 1260 spectrum impedance analyzer showed a phase angle of close to −90°, but not exactly at −90°, indicative that the current flow had a small resistive component, i.e., within the definition of the lossy dielectric properties of electrodes of the present invention. The testing voltage used was less than 3 volts but the the actual current density was similar to the actual current density generated by the electrosurgical generator.

Therefore, the electrically insulative paint was acting as a lossy dielectric layer as defined according to the present invention, which at high electrosurgical power output was permitting passage of current in a very limited resistive manner, i.e., in the manner of a lossy dielectric capacitor.

EXAMPLES 15–19 AND COMPARATIVE EXAMPLE 20

Additional electrodes corresponding to the electrodes of Examples 2–6 were made and tested using an Agema 470 Infra Red camera to measure temperature quantitatively. Testing of the electrodes found that the area of highest temperature rise during usage was very sharply confined to the corners of the electrode.

As a control (Comparative Example 20), a standard resistive-type electrode was prepared without any paint as a lossy dielectric layer and having a 129 $cm^2$ (20 square inch) (with 2.54 cm radiused corners). For this control electrode to have a 4° C. maximum temperature rise, the portion of the electrode having an increase of from 3°–4° C. represented only about 2–4% of the total surface area of the electrode. Thus, a temperature reduction of 25% was achievable, if the heat in the corners could be reduced, with no other reduction in edge effect.

Electrodes were produced according to Examples 2–6 with a painted border that was wider by 1.35 cm at the corners of the electrode than at the middle of each edge and with different coating weights of paint being knife coated on the Al foil (3, 6, 9, 13, and 17 grains/4 in.×6 in. (10.2×15.2 cm) Examples 15–19, respectively). Besides providing a high impedance layer at the edge of the electrode to drive current distribution inward, the wider corners drove the current from the corners laterally towards the middle of each edge.

The area between the square and circle was then cut out, and the open area in the middle of the plate was filled with a second thickness of Al foil. Both layers were then laminated to a layer of the same conductive adhesive as used in prior examples. These electrodes were then tested using the same AAMI standard on the anterior thighs of the same human.

Figure 4:
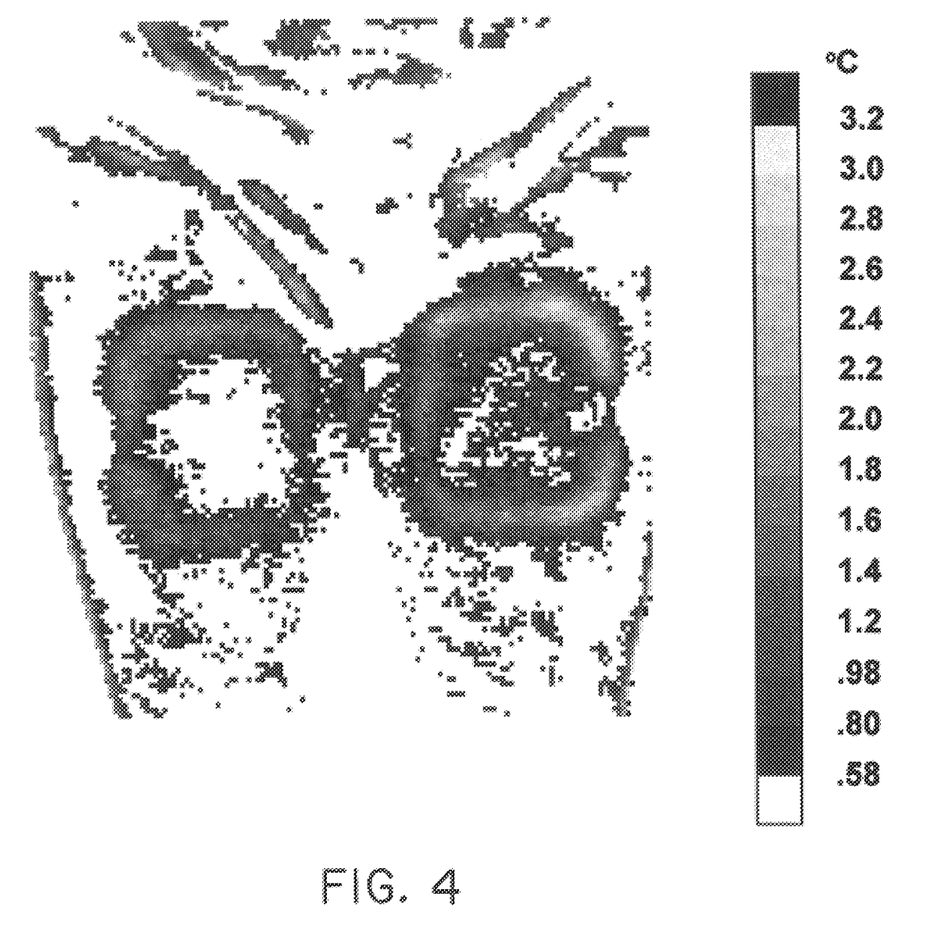
FIG. 4 shows comparative subtracted thermograms of a dispersive electrode of the prior art and a dispersive electrode of the present invention.

FIG. 4 shows the thermogram results with the electrode on the right thigh (left side of photograph) being the electrode of Example 17 and the electrode on the left thigh (right side of photograph) being an electrode of Comparative Example 20 having a surface of 129 $cm^2$ (20 square inch).

As the coating weight of the paint increases, the area of maximum current density (and temperature in tissue of the patient beneath the electrode) of Examples 15–19 shifts from the outer corners of the electrode in toward the bare Al foil center of the electrode. More importantly, at a coating weight in about the middle of the range of coating weights used (Example 17, 9 grains), a much more diffuse heat distribution was noted, as seen in FIG. 4. Table 1 shows the results.

TABLE 1

| Example | Coating Wt. (grains) | Max. Tissue Temp. Rise vs. Comp. Example 20 (°C.) |
| --- | --- | --- |
| 15 | 3 | −0.4 |
| 16 | 6 | −0.5 |
| 17 | 9 | −0.6 |
| 18 | 13 | −0.1 |
| 19 | 17 | −0.2 |
| Comp. 20 | None | — |

More importantly, at a coating weight in about the middle of the range of coating weights tried, (i.e., about 9 grains), the increase in maximum temperature at the corners and at the edges is both reduced and more evenly distributed.

EXAMPLES 21–22

Electrodes from Examples 15–19 were reproduced, except that the width of the painted border at the middle of each edge was increased from 0.95 cm (¼") to 1.3 cm (½") to 1.9 cm (¾"). Table 2 shows the results. With the width of the border increasing, the net temperature reduction was not as great.

TABLE 2

| Example | Width of Painted Border (cm) | Max. Tissue Temp. Rise vs. Comp. Example 20 (°C.) |
|---|---|---|
| 17 | 0.95 | −0.6 |
| 21 | 1.3 | −0.2 |
| 22 | 1.9 | 0.5 |

COMPARATIVE EXAMPLES 23 AND 24

Figure 5:
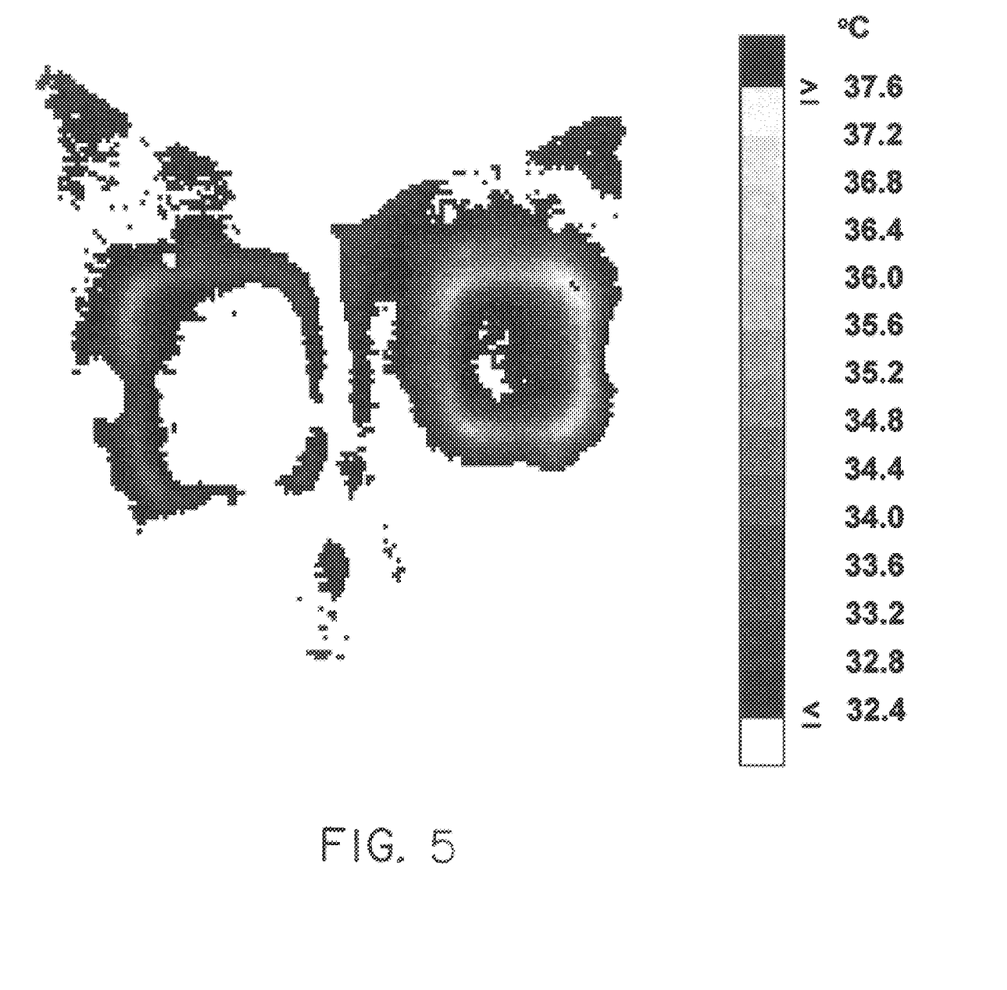
FIG. 5 shows comparative thermograms of dispersive electrodes.
Figure 6:
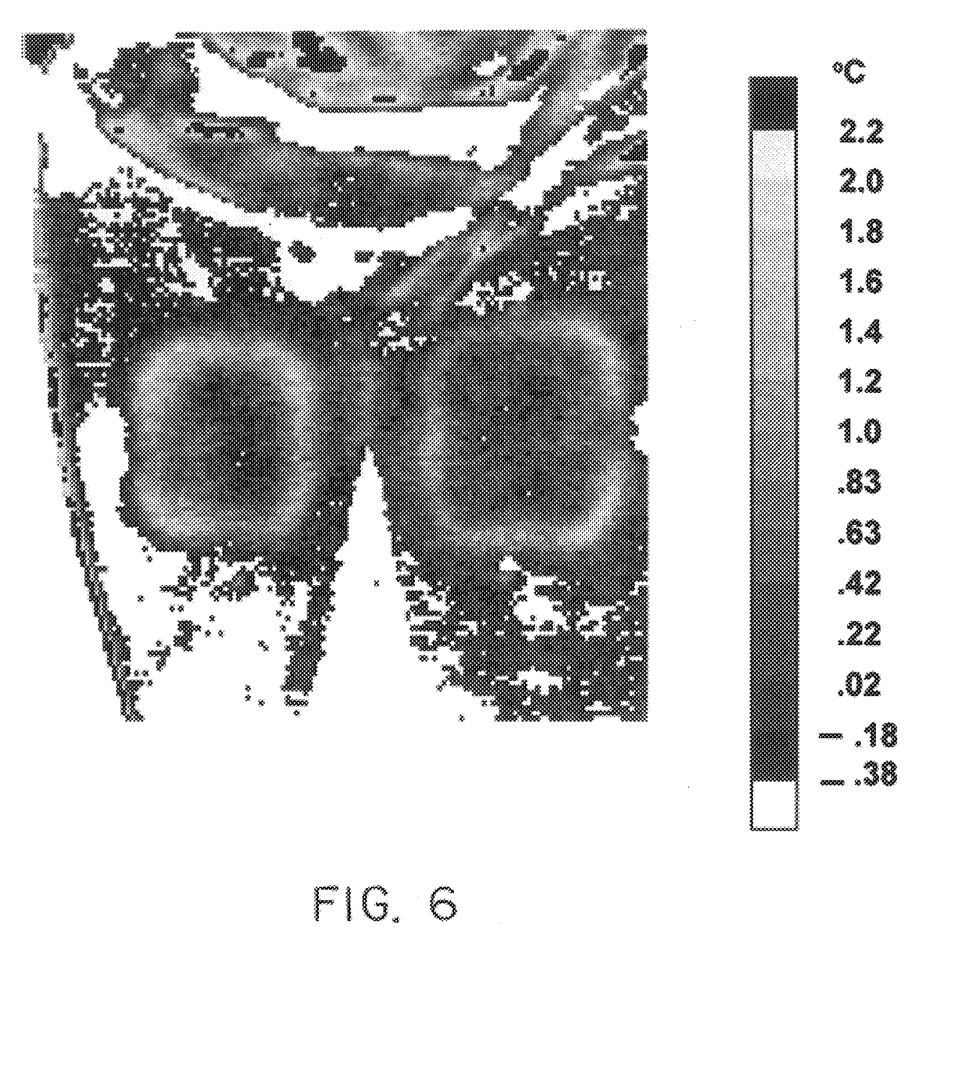
FIG. 6 shows comparative subtracted thermograms of a dispersive electrode of the prior art and a dispersive electrode of the present invention.

To contrast the lossy dielectric properties of electrodes of the present invention with materials known to act as pure dielectric materials, two constructions were made up similar to those Examples 8–14, except that an acrylate pressure sensitive adhesive (PSA) having a formulation of isooctyl acrylate/acrylic acid in a ratio of 96:4 and a 0.1 mm (0.47 mil) PET film were each substituted for the paint. In Comparative Example 23, only the thinnest layer obtainable of acrylate adhesive (0.025 mm) was used in an attempt to create lossy dielectric properties using a truly dielectric material. In Comparative Example 24, a combination of the acrylate adhesive and the PET film was used. The results are shown FIG. 5. The current is sharply concentrated at the outer edge of the bare metal in the center of the plate. This is further indication that the electrically insulating paint is acting as something less than a good dielectric, since the thermogram results seen in FIG. 5 are inferior to the thermogram results seen in FIG. 5, even with the heaviest coating weight (17 grains) of paint.

In other words, a very thick layer of paint still does not force the current to the center as much as the thinnest layer of acrylate adhesive available. As such, the paint cannot be considered to be a true dielectric material like the acrylate adhesive and PET film and becomes a preferred material to provide lossy dielectric properties for the dispersive electrode.

EXAMPLES 25–29 AND COMPARATIVE EXAMPLE 30

Having thus established that the current distribution on a 129 cm² (20 square inch) electrode was made more even by the use of a lossy dielectric material coating the outer edge of an aluminum electrode, an electrode of this construction but smaller in area was made to demonstrate that the smaller electrode yielded a maximum temperature rise similar to a conventional dispersive electrode.

An electrode was produced having a conductor area of 97 cm² (15 square inches). Paint (No. 7715 from Rustoleum) was coated around the edges at 5 different coating weights (1, 2, 3, 5, and 7 grains/10.2 cm×15.2 cm (4×6), (Examples 26–30, respectively) and electrodes were prepared and tested in the same manner as the above Examples. The results are shown in Table 3 below and in FIG. 6 where left thigh-right side electrode is Comparative Example 31 and the right thigh-left side electrode is Example 27. Using 3 grains of paint, the maximum temperature rise for the Example 27 electrode was no greater than the control Comparative Example 31 prepared in the same manner as Comparative Example 20.

TABLE 3

| Example | Coating Wt. (grains) | Max. Tissue Temp. Rise vs. Comp. Example 30 (°C.) |
|---|---|---|
| 25 | 1 | 0.8 |
| 26 | 2 | 0.2 |
| 27 | 3 | 0.0 |
| 28 | 5 | 0.4 |
| 29 | 7 | 0.5 |
| Comp. 30 | None | — |

Using a lossy dielectric material on electrodes of the present invention permitted a substantial size reduction (25% decrease in area) without a significant increase in maximum tissue temperature greater than the increase in maximum tissue temperature of a conventional, resistive electrosurgical dispersive electrode having a conductor area of about 129 cm (20 sq. in.). For the electrode of Example 27, the 25% decrease in area did not create any increase in maximum tissue temperature.

The present invention permits one skilled in the art to construct a lossy dielectric electrode having the same or smaller temperature rise with a smaller sized electrode or a smaller temperature rise with a same sized electrode. A dispersive electrode of smaller size can be significantly less expensive to make.

EXAMPLES 31–58 AND COMPARATIVE EXAMPLES 59–65

The electrodes of Examples 15–19 were reproduced, except that a variety of different coating weights and paints and inks were employed. A variety of commercially available dispersive electrodes were gathered. Impedance (Z)/area (Ω/129 cm²) resistance (R)/area (Ω/129 cm²), reactance (X) /area (Ω/129 cm²), tan δ, and δ(°) were measured. Table 4 shows the results.

TABLE 4

| Example | Lossy Dielectric Layer | Coat. Wt. (Grains/ 4" × 6" | Z/area (Ω/129 cm²) | R/ area (Ω/129 cm²) | X/area (Ω/129 cm²) | tan δ | δ (°) |
|---|---|---|---|---|---|---|---|
| 31 | 7790 | 2.75 | 2.020 | 0.702 | −1.898 | 0.370 | 20.285 |
| 32 | 7790 | 6.96 | 5.360 | 1.024 | −5.265 | 0.195 | 11.010 |
| 33 | 7790 | 9.32 | 7.420 | 1.066 | −7.347 | 0.145 | 8.250 |
| 34 | 7790 | 13.08 | 10.340 | 1.189 | −10.268 | 0.116 | 6.610 |
| 35 | 7790 | 18.1 | 14.080 | 1.563 | −13.993 | 0.112 | 6.370 |
| 36 | 7776 | 3.280 | 2.710 | 0.778 | −2.599 | 0.299 | 16.654 |
| 37 | 7776 | 6.050 | 4.450 | 0.744 | −4.383 | 0.170 | 9.636 |

TABLE 4-continued

| Example | Lossy Dielectric Layer | Coat. Wt. (Grains/ 4" × 6") | Z/area (Ω/129 cm$^2$) | R/ area (Ω/129 cm$^2$) | X/area (Ω/129 cm$^2$) | tan δ | δ (°) |
|---|---|---|---|---|---|---|---|
| 38 | 7776 | 9.530 | 7.460 | 0.929 | −7.406 | 0.125 | 7.146 |
| 39 | 7776 | 12.760 | 9.900 | 1.021 | −9.849 | 0.104 | 5.919 |
| 40 | 7730 | 1.700 | 2.150 | 0.618 | −2.062 | 0.300 | 16.676 |
| 41 | 7730 | 2.970 | 4.320 | 0.826 | −4.237 | 0.195 | 11.034 |
| 42 | 7730 | 6.080 | 7.990 | 0.955 | −7.931 | 0.120 | 6.865 |
| 43 | 7730 | 8.830 | 12.080 | 1.207 | −12.022 | 0.100 | 5.731 |
| 44 | 7730 | 11.830 | 16.240 | 1.573 | −16.160 | 0.097 | 5.558 |
| 45 | 7727 | 1.510 | 3.100 | 0.716 | −3.016 | 0.237 | 13.353 |
| 46 | 7727 | 1.950 | 3.910 | 0.881 | −3.807 | 0.231 | 13.026 |
| 47 | 7727 | 3.690 | 7.740 | 1.307 | −7.634 | 0.171 | 9.712 |
| 48 | 7727 | 5.500 | 11.170 | 1.299 | −11.095 | 0.117 | 6.678 |
| 49 | 7727 | 7.550 | 15.160 | 1.658 | −15.073 | 0.110 | 6.277 |
| 50 | 7715 | 1.150 | 1.360 | 0.687 | −1.178 | 0.584 | 30.272 |
| 51 | 7715 | 1.680 | 1.580 | 0.590 | −1.462 | 0.404 | 21.976 |
| 52 | 7715 | 3.080 | 2.440 | 0.675 | −2.342 | 0.288 | 16.077 |
| 53 | 7715 | 4.880 | 3.180 | 0.702 | −3.099 | 0.226 | 12.755 |
| 54 | 7715 | 6.590 | 4.010 | 0.847 | −3.918 | 0.216 | 12.204 |
| 55 | 800 | 1 pass | 4.670 | 1.121 | −4.535 | 0.247 | 13.887 |
| 56 | 800 | 2 pass | 9.630 | 2.685 | −9.246 | 0.290 | 16.192 |
| 57 | 801 | 1 pass | 4.180 | 0.758 | −4.108 | 0.185 | 10.461 |
| 58 | 801 | 2 pass | 8.970 | 1.444 | −8.854 | 0.163 | 9.260 |
| C-59 | Coraplate | | 33.205 | 5.346 | −32.772 | 0.163 | 9.264 |
| C-60 | Elmed | | 61.529 | 4.689 | −61.350 | 0.076 | 4.371 |
| C-61 | Mera SAS | | 64.004 | 4.576 | −63.840 | 0.072 | 4.099 |
| C-62 | Diatemp II | | 47.747 | 2.581 | −47.678 | 0.054 | 3.098 |
| C-63 | 0.05 PET | | 46.030 | 2.781 | −45.945 | 0.061 | 3.464 |
| C-64 | 3M 7149 | | 0.516 | 0.387 | 0.258 | 1.809 | 61.07 |
| C-65 | 3M 7146 | | 1.302 | 1.302 | 0.516 | 2.242 | 65.96 |

7790, 7776, 7730, 7727, and 7715 are all Rustoleum branded enamel paints.
800 and 801 are both Summit branded white inks.
Coraplate is a capacitive dispersive electrode commercially available from Cora-vertrieb of Mainz, Germany
Elmed is a capacitive dispersive electrode commercially available from Elmed of Addison, Illinois
Mera SAS is a capacitive dispersive electrode commercially available from Mera of Tokyo, Japan
Diatemp II is a capacitive dispersive electrode commercially available from NDM of Dayton, Ohio
0.05 PET is an experimental dispersive electrode prepared according to the disclosure of U.S. Pat. No. 4,387,714 (Geddes et al.)
3M 7149 and 7146 are resistive dispersive electrodes commercially available from 3M Company, St. Paul, MN.

As seen by an analysis of the data shown in Table 4, the variety of coating weights and paints and inks to generate lossy dielectric layers on electrically conductive surfaces result in biomedical electrodes that neither function like capacitive electrodes (Comparison Examples C-59–C-63) nor function like resistive electrodes (Comparison Examples C-64 and C-65).

All test results shown in Table 4 are normalized to unit area or dimensionless values. Therefore, one skilled in the art can readily determine how it is possible to control the extent of lossy dielectric properties on biomedical electrodes for either electrosurgical or cardiac stimulation uses.

One should strive to obtain a value of tan δ in the range approaching a pure capacitive biomedical electrode (~0) (as in Comparison Examples C-59–C-63) while also striving to limit Z/area as much as possible (as in Comparison Examples C-64 and C-65). Only biomedical electrodes of the present invention with lossy dielectric properties as described above succeed in providing both low tan δ values and low Z/area values.

Variations in the invention have also employed several types of paints and printing inks as lossy dielectrics materials, serving to achieve the twin goals of reduced edge effect and size reduction in electrodes. With appropriate thinness of any dielectric material, that material could be made to act as a lossy dielectric and be used in the construction of the electrode of the present invention.

Further shapes other than squares with inscribed circles can be made to work using the present invention, as well as means other than knife coating (screen printing, gravure printing, ink bubble jet technology, etc.) can be used to create or deposit a lossy dielectric layer on a conductive substrate.

Further, multiple areas around the outer edge of an electrode can be coated with different thicknesses of paint or with different types of paint or ink to provide gradual "shading" of the lossy dielectric material. While not necessary for the advantages of the present invention, a gradual shading technique can optimize the performance of the electrode.

Other methods of creating the effects of the lossy dielectric properties for a dispersive electrode of the present invention include (a) the addition of a sheet or scrim of a lossy dielectric material in the field of conductive adhesive 32 rather than to the electrically conductive surfaces 14 and 16; (b) the addition of a lossy dielectric, pressure-sensitive adhesive coated sheet or film to the field 32 of conductive adhesive on at least a portion of the skin contacting surface; and means of altering (by photochemistry, electrochemistry, or otherwise) to impart lossy dielectric properties on a portion of electrically conductive surfaces 14 or 16 or in a portion of field 32.

The choices available to one skilled in the art because of the breadth of the present invention permit construction of electrodes using a simple and cost-effective means of production, which can yield a product that can be commercially produced in preference to a construction that requires multiple conductive elements, layers, or pieces. A smaller electrode with the same performance characteristics will require less raw materials to make, and be more convenient for use by the customer at the same time.

Various modifications and alterations of the present invention will be apparent to those skilled in the art without departing from the scope and spirit of this invention, and it should be understood that this invention is not limited to the illustrative embodiments set forth herein. The claims follow.

What is claimed is:

1. A biomedical electrode, comprising:
   an electrically non-conductive backing;
   a conductive plate contacting the electrically non-conductive backing, wherein the conductive plate has a body contacting portion, wherein the body contacting portion has an exterior edge and a region adjacent the exterior edge;
   a field of lossy dielectric material contacting the region adjacent the exterior edge; and
   a field of conductive adhesive in contact with both the conductive plate and the field of lossy dielectric material and adapted to adhere the electrode to a body of a patient.

2. The biomedical electrode according to claim 1 wherein the conductive plate has an extended tab.

3. The biomedical electrode of claim 2, wherein the lossy dielectric material occupies an area of the body contacting portion ranging from about 5% to about 70%.

4. The biomedical electrode of claim 2, wherein the lossy dielectric material has a maximum impedance per 129 $cm^2$ at the exterior edge of the body contacting portion ranging from about $0.387\Omega/129$ $cm^2$ to about $20\Omega/129$ $cm^2$.

5. The biomedical electrode according to claim 1 further comprising a second conductive plate, wherein the field of lossy dielectric material contacts only a portion of each of the conductive plates.

6. The biomedical electrode according to claim 5 wherein the each of the conductive plates has a body contacting portion and an extended tab and wherein the field of lossy dielectric material contacts a region adjacent the exterior edge of the body contacting portion of each conductive plate.

7. The biomedical electrode of claim 3, wherein two different fields of conductive adhesive contact the two different conductive plates.

8. The biomedical electrode according to claim 1 wherein the field of lossy dielectric material has performance parameters between the extremes of:
   a resistive-type dispersive electrode that causes an edge effect at a periphery of a conductive surface; and
   a capacitive-type dispersive electrode that causes only capacitive flow between the conductive surface and the body of a patient.

9. The biomedical electrode of claim 8, wherein the lossy dielectric material minimizes the maximum amount of temperature rise in tissue of a patient in contact with the biomedical electrode of a geometry compared with a resistive-type dispersive electrode of the same geometry.

10. The biomedical electrode of claim 9, wherein the amount of tissue maximum temperature rise is less than about 6° C. from beginning of usage with an electrosurgical generator when tested according to AAMI Standard Section 4.2.3.1 (1986).

11. The biomedical electrode of claim 1, wherein regions of the electrode have a reactance per 129 $cm^2$ ranging from about $-0.5\Omega/129$ $cm^2$ to about $-16\Omega/129$ $cm^2$ at the exterior edge on the electrode.

12. The biomedical electrode of claim 1, wherein regions of the electrode have a tan δ ranging from about 0.14 to about 1.7 at the exterior edge of the body contacting portion, measured at 500 kHz and a signal amplitude of 60 mV (RMS).

13. The biomedical electrode of claim 1, wherein the lossy dielectric material has an impedance/area of from about $0.387\Omega/129$ $cm^2$ to about $20\Omega/129$ $cm^2$ at the exterior edge of the body contacting portion; and a tan δ ranging from about 0.1 to about 1.7 at the exterior edge of the body contacting portion, measured at 500 kHz and a signal amplitude of 60 mV (RMS).

14. The biomedical electrode of claim 1, wherein the lossy dielectric material has an impedance/area of from about $1\Omega/129$ $cm^2$ to about $8\Omega/129$ $cm^2$ at the exterior edge of the body contacting portion; and a tan δ ranging from about 0.2 to about 0.7 at the exterior edge of the body contacting portion on the biomedical electrode, measured at 500 kHz and a signal amplitude of 60 mV (RMS).

15. An electrosurgical system, comprising:
   an electrosurgical generator and a biomedical electrode connected to the electrosurgical generator, wherein the biomedical electrode comprises an electrically non-conductive backing;
   a conductive plate contacting the electrically non-conductive backing, wherein the conductive plate has a body contacting portion, wherein the body contacting portion has an exterior edge and a region adjacent the exterior edge;
   a field of lossy dielectric material contacting the region adjacent the exterior edge; and
   a field of conductive adhesive in contact with both the conductive plate and the field of lossy dielectric material and adapted to adhere the electrode to a body of a patient.

16. A method of making a biomedical electrode, comprising the steps of:
   (a) applying a lossy dielectric material to at least a portion of a conductive surface and;
   (b) contacting a field of conductive adhesive to both the conductive surface and the lossy dielectric material.

17. The method of claim 16, wherein the step of applying comprises coating a portion of the conductive surface with the lossy dielectric material.

18. The method of claim 17, wherein the field of lossy dielectric material is applied in a manner to provide an electrical impedance gradient from a center of the conductive surface to an exterior edge of the conductive surface ranging from about 30% to about 90% of maximum impedance at the exterior edge.

* * * * *